United States Patent [19]

Watanabe et al.

[11] 4,171,429

[45] Oct. 16, 1979

[54] PYRIMIDINE TO PYRIMIDINE TRANSFORMATION PROCESS

[75] Inventors: Kyoichi A. Watanabe, Port Chester; Kosaku Hirota, Mamaroneck; Chung K. Chu, Port Chester; Uri Reichman, New Rochelle; Jack J. Fox, White Plains, all of N.Y.

[73] Assignee: Research Corporation, New York, N.Y.

[21] Appl. No.: 782,353

[22] Filed: Mar. 29, 1977

[51] Int. Cl.[2] .............. C07D 239/46; C07D 239/56; C07D 407/04; C07H 19/06
[52] U.S. Cl. ........................................ 536/1; 424/180; 424/251; 544/309; 544/314; 544/320
[58] Field of Search ................... 260/256.4 C, 251 R, 260/260; 536/1; 544/309, 314, 320

[56] References Cited

PUBLICATIONS

Shugar et al., Biochem. Biophys. Acta., vol. 9, pp. 199–215 (1952).

*Primary Examiner*—Alton D. Rollins
*Attorney, Agent, or Firm*—Omri M. Behr

[57] ABSTRACT

There is provided a novel process for pyrimidine to pyrimidine transformations by the displacement of the 1,2,3-portion of a pyrimidine by a 1,3-ambident nucleophile. The novel process requires that the 1 and 3 nitrogens of the pyrimidine moiety be substituted. The novel process makes available, inter alia, novel uracils, simple methods of radioisotopically labeling pyrimidine nuclei, a simple and inexpensive method of preparing the important antiviral and antileukemic material pseudoisocytidine and its new active analog 2'-deoxypseudoisocytidine.

9 Claims, No Drawings

PYRIMIDINE TO PYRIMIDINE TRANSFORMATION PROCESS

The work upon which the present invention is based was supported by grants from the National Cancer Institute, National Institutes of Health, U.S. Public Health Service, Department of Health, Education and Welfare.

DESCRIPTION OF THE PRIOR ART

Ring transformations of pyrimidines with various nucleophilic reagents is well known. For example, the transformation of pyrimidines to pyrazoles or oxazoles with hydrazine or hydroxylamine has been extensively employed in nucleic acid modification (Kochetkov et al, Progr. Nucleic Acid Res. Mol. Biol., 9 403 (1969); Ueda and Fox, Adv. Carbohyd. Chem., 22, 307 (1967)). Heretofore, such transformations utilizing 1,3-ambident nucleophiles such as guanidine, urea, or thiourea have not been reported and, indeed, in the hands of the Applicants hereof, uracil did not react with these nucleophiles.

The instability of 1,3-dimethyluracil in mild base was reported by Shugar and Fox (Biochem. Biophys. Acta, 9, 199 (1952). The reason for this instability has not heretofore been postulated.

SUMMARY OF THE INVENTION

There is provided a novel process for transforming N.N-di-substituted 1,3-pyrimidines of the formula I

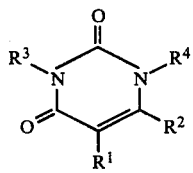

wherein $R^1$ is hydrogen, halogen, alkyl, aralkyl or aryl or a saccharide moiety, $R^2$ has the same value as $R^1$ provided that $R^1$ and $R^2$ are not both saccharide moieties, $R^3$ and $R^4$ are alkyl or aralkyl.

Into a pyrimidine of the formula II

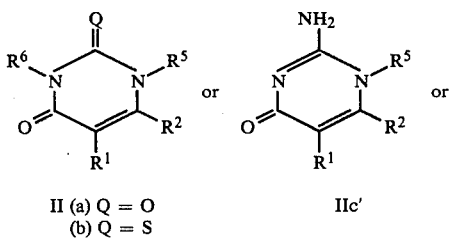

II (a) Q = O
(b) Q = S

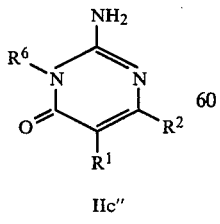

IIc'' wherein $R^1$ and $R^2$ are as above, $R^5$ and $R^6$ may be the same or different and are hydrogen or have the same meaning as $R^3$ and Q is O, S, or NH.

The transformation is achieved by reacting the pyrimidine of Formula I with a nucleophile of the formula

III (a) Q = O
(b) Q = S
(c) Q = NH wherein Q, $R^5$ and $R^6$ are as defined above in a basic environment, provided that where Q is —NH, either $R^5$ or $R^6$ must be hydrogen. Where $R^5$ and $R^6$ are different, especially where one of these moieties is hydrogen, the possibility of isomerism exists. It has been found that in this latter case, isomer ratio is heavily in favor of 1-substitution. Where Q=NH tautomerization is also possible—i.e., IIc' or IIc''. Where $R^5=R^6=H$, it has been found that the tautomers IIc' and IIc'' exist in substantially equal proportions.

This basic environment is provided either where the nucleophile is itself a strong base—for example, where the nucleophile is guanidine—or by the provision of an external base—for example, an alkali metal alkoxide in a suitable alkanol.

The reaction is influenced, not only by the basicity of the reaction medium, but also by the nature of the substitution pattern on the pyrimidine nucleus. The absence of hydrogen atoms on the two ring nitrogens is a requirement of the reaction process; however, where $R^1$ and $R^2$ are both hydrogen, or where $R^1$ is halogen, the reaction proceeds very readily in rather mild conditions. On the other hand, where $R^1$ carries an alkyl or saccharide moiety, more vigorous conditions are required. Similarly, while an alkyl substituent at $R^2$ will retard the ease of transformation, such a retardation is totally overcome by the presence of a halogen substituent at $R^1$.

The process of the present invention has wide ranging utility. The reaction, when carried out with urea, or substituted urea, which does not substantially alter the chemistry of the product as opposed to the starting material, provides a very simple way of radioisotopically labeling the pyrimidine nucleus. It provides a ready method of converting the readily obtainable uracils into analogs thereof which are more difficult of synthesis and it provides a route to the 5-glycosyl derivatives of uracil and analogs thereof which have utility as antiviral agents and, in some cases, compounds such as pseudoisocytidine (Chu et al, J. Org. Chem., 41, 2793 [1976]) and the newly available (by this process) novel compound 2'-deoxypseudocytidine, which also possess useful antitumor activity.

DESCRIPTION OF THE PREFERRED EMBODIMENTS

The preferred starting materials of the process of the present invention are subsumed under general Formula I as follows:

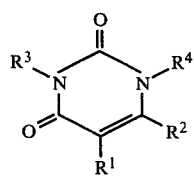

$R^1$ may be hydrogen, halogen, suitably fluorine, chlorine or bromine, alkyl, suitably lower alkyl of 1 to 5 carbon atoms such as methyl, ethyl, propyl, isopropyl, butyl, isobutyl, tert.-butyl, pentyl, and the like. The designation of alkyl, however, is not to be considered as limited to lower alkyl although the most commonly available substituent will be found in the lower alkyl grouping. $R^1$ may also be aralkyl, suitably, aryl lower alkyl, preferably phenyl lower alkyl, wherein the phenyl moiety may additionally be substituted by alkyl, alkoxy, or halo moieties. $R^1$ may also be aryl, suitably phenyl, wherein the phenyl moiety may, if desired, be substituted as immediately hereintofore. Among the most preferred embodiments of $R^1$ is that where $R^1$ is a saccharide residue, suitably a pentosyl moiety, especially a ribosyl or arabinosyl moiety. Included within the scope of these moieties are the 2'-deoxy moieties wherein the hydroxyl group normally at the 2'-position on the pentosyl ring is replaced by a hydrogen.

$R^2$ has the same values as $R^1$; however, $R^1$ and $R^2$ may not, at the same time, have a saccharide meaning.

$R^3$ and $R^4$ are substantially non-labile substituent groups. The nature of $R^3$ and $R^4$ is not important provided that they are not readily replaced under the reaction conditions by hydrogen. The purpose of the substitution of the 1 and 3 nitrogen groups is to remove the labile hydrogen thereof. Thus, any base stable substituent would be operative. Thus, $R^3$ and $R^4$ are conveniently alkyl or aralkyl, wherein alkyl may be lower alkyl of 1 to 5 carbon atoms, aralkyl may suitably be phenyllower alkyl wherein the lower alkyl has 1 to 5 carbon atoms. For reasons of cost, the most convenient substituents are methyl, ethyl and benzyl, and of these methyl is especially to be preferred.

The starting materials of the present process are then reacted with a nucleophile of the general Formula III

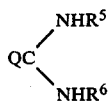

wherein $R^5$ and $R^6$ may be the same or different and may be hydrogen or have the same values as $R^3$ above. Q may be oxygen, sulfur, or NH, provided that where Q is NH, either $R^5$ or $R^6$ must be hydrogen.

While a common factor in the process is that it shall be carried out in basic conditions, the range of intensity of reaction conditions will vary depending upon the substitution pattern of the pyrimidine ring and the basicity of the nucleophile. Thus, in the optimum circumstance, where the pyrimidine is highly susceptible to nucleophilic attack—for example, where $R^1$ is fluoro and $R^2$ is hydrogen together with the use of a very basic nucleophile such as guanidine—the transformation will take place utilizing a substantial excess of guanidine, say, a 5 to 10, suitably a 7, molar excess of guanidine in a refluxing polar solvent, in a period of from about 6 to about 12 hours. The solvent utilized need not be limited to ethanol. Among other solvents may be mentioned other alkanols such as methanol or butanol.

Where the substitution pattern is unfavorable, as, for example, the case of 1,3,-dimethylpseudouridine which is converted to pseudoisocytidine, the reaction is suitably carried out by heating the starting material in fusion with liquified guanidine at a temperature of between 60° and 100° C., suitably between 80° and 90° C.

In the least favorable situation—that is to say, where the substitution pattern is unfavorable and the nucleophile is a weak base—the reaction is suitably carried out as stated before in a suitable refluxing alkanol in the presence of the corresponding (to the alkanol) alkali metal alkoxide—for example, sodium ethoxide. It has been found suitable to use an approximately equimolar amount of base per mole of pyrimidine.

Upon completion of the reaction, the reaction mixture is quenched, suitably by pouring the reaction mixture into an excess of water—a 10 to 20 column excess is considered to be suitable. The isolation of product II depends on the nature of Q in the ambident nucleophile III employed and the presence of absence of a saccharide moiety on C-5. Thus, where urea or 2-thiourea is employed on pyrimidines (I) without a saccharide moiety on C-5, the aqueous solution is acidified with hydrochloric acid to $\sim$ pH 2 whereupon precipitation of product (IIa) or (b) occurs.

When guanidine is employed (IIIc, Q=NH) and the pyrimidine (I) does not bear a saccharide moiety on C-5, the aqueous solution is neutralized to $\sim$ pH 7–8 whereupon the isocytosine derivative (IIc' or IIc'') precipitates out.

When the starting pyrimidine (I) bears a saccharide moiety on C-5 and guanidine is employed as the ambident nucleophile (and while the invention is in no way limited thereto), the aqueous solution is passed through an Amberlite IRC-50 (H+) resin (Amberlite is a trademark of Rohm and Haas, Inc., Philadelphia, Pennsylvania) or any acid phase ion exchange resin having substantially similar properties thereto. Removal of the water affords a syrup which is crystallized from ethanol to yield pseudoisocytidine (IIc) as the free base. Alternatively, the syrup is dissolved in methanol and treated with methanolic hydrogen chloride. Pseudoisocytidine hydrochloride precipitates out.

Lastly, when starting material (I) where $R^1$ is a saccharide is refluxed in ethanol with thiourea in the presence of sodium ethoxide, product (IIb) ($R^1$=ribofuranosyl; $R^2$, $R^5$ and $R^6$=H; Q=S) precipitates as the sodium salt directly from the reaction mixture.

It will be understood by those skilled in the art that the starting pyrimidines utilized in the novel process of the present invention are not usually available in the 1,3-di-substituted form.

As stated hereinabove, the nature of the substituent on the two ring nitrogen is not particularly important provided that they are not labile under the conditions of the principal process. It has been found particularly suitable to methylate these two nitrogens and such methylation can be readily achieved by taking up the pyrimidine (I) in dimethylformamide dimethylacetal and heating under reflux for from between 0.5 to about 2 hours. The solvent is then removed under reduced pressure to yield the N,N-dimethylated product in a form of purity sufficient to carry out the principal reaction.

All Temperatures are in °C.

EXAMPLE I

Isocytosine from 1,3-Dimethyluracil (a) Guanidine hydrochloride (IIIc) (10 g, 0.1 mol) was added to 1 M sodium ethoxide (100 ml) and the mixture was stirred for 10 minutes at room temperature after which the mixture was filtered quickly from sodium chloride. To the filtrate was added 1,3-dimethyluracil (1.4 g, 0.01 mol) and the mixture refluxed for 18 hours under nitrogen. The solvent was removed by evaporation under reduced pressure and the syrupy residue dissolved in water (30 ml). The solution was passed through a column of Amberlite IRC-50 (H+) and the column washed with water. The uv absorbing fractions were combined and evaporated in vacuo to dryness to a syrup which crystallized upon trituration with ethanol. The yield of isocytosine (IIIc, $R^1$, $R^2$=H) was 0.73 g (66%), mp 265°–267°. A mixed melting point with an authentic sample of isocytosine was not depressed. The uv and ir spectrum of the product was identical with that for isocytosine.

In accordance with the above procedure but where, in place of 1,3-dimethyluracil, there is employed 1,3-diethyluracil, 1,3-ditertbutyluracil or 1,3-dibenzyluracil there is obtained the same product.

(b) Preparation of 1,3-dimethyluracil from uracil

A suspension of uracil (1 g) in dimethylformformamide dimethylacetal is heated under reflux until a clear solution is obtained. This solution is concentrated to a syrup and triturated with acetone to yield a solid which is recrystallized from ethanol to yield 1,3-dimethyluracil.

EXAMPLE II

5-Fluoroisocytosine from 1,3-Dimethyl-5-fluorouracil

Guanidine hydrochloride (IIIc) (10 g, 0.1 mol) was added to 1 M ethanolic sodium ethoxide (100 ml) and the mixture was stirred for 10 minutes at room temperature. Sodium chloride was removed from the mixture by filtration. To the filtrate was added 1,3-dimethyl-5-fluorouracil (1.6 g, O.01 mol) and the mixture was refluxed for 8 hours under nitrogen after which the solvent was removed by evaporation in vacuo. The residue was dissolved in water (20 ml) and the solution passed through a column of Amberlite IRC-50 (H+) (30×3 cm diameter) to remove excess guanidine. The column was washed with water and the uv absorbing fractions collected and concentrated to dryness in vacuo. The residue which contained 5-fluoroisocytosine and 1,3-dimethyluracil was dissolved in methanol (5 ml) and chromatographed over a column of silica gel 60 (30×3 cm diameter) using chloroform-methanol (9:1) as the eluent. The uv absorbing fractions were combined and evaporated to dryness under reduced pressure. The solid residue was recrystallized from water to give 230 mg of 5-fluoroisocytosine (IIc, $R^1$=F, $R^2$=H) mp 274°–276° dec. [Biressi et al., Gazz. Chim. Ital. 93, 1269 (1963) reported mp 271°–274°]. The uv characteristics of this sample were identical to those reported for 5-fluorisocytosine [Wempen and Fox, J. Med. Chem., 6, 688 (1963)].

In accordance with the above procedure but where, in place of 1,3-dimethyl-5-fluorouracil, there is used 1,3-dimethyl-5-chlorouracil, there is obtained 5-chloroisocytosine.

In accordance with the above procedure but where, in place of guanidine hydrochloride and 1,3-dimethyl-5-fluorouracil, there is employed guanidine hydrochloride and 1,3-dimethyl-5-phenyluracil, there is obtained 5-phenylisocytosine.

EXAMPLE III

6-Methylisocytosine from 1,3,6-Trimethyluracil

Guanidine hydrochloride (IIIc) (10 g, 0.1 mol) was added to 1 M ethanolic sodium ethoxide (100 ml) and the mixture was stirred for 10 minutes at room temperature. Sodium chloride was removed from the mixture by filtration, and the filtrate was condensed to a syrup in vacuo below 35°. To the residue was added 1,3,6-trimethyluracil (800 mg, 0.005 mol) and the mixture was heated at ~90° for 6 hours under nitrogen. The reaction mixture was dissolved in water (20 ml) and the solution added to a column of Amberlite IRC-50 (H+) (30×3 cm diameter) and the column was washed with water. The uv absorbing fractions were collected and evaporated to dryness in vacuo. The solid residue was recrystallized from water to give 6-methylisocytosine (IIb, $R^1$=H, $R^2$=methyl) (320 mg, mp 290°–292° dec.). The uv and ir characteristics were identical with those of an authentic sample of 6-methylisocytosine.

In accordance with the above procedure, but where in place of 1,3,6-trimethyluracil there is employed 1,3,5-trimethyluracil or 1,3-dimethyl-5-benzyluracil, there is obtained the corresponding 5-methylisocytosine or 5-benzylisocytosine.

EXAMPLE IV

2-Thiouracil from 1,3-Dimethyluracil 1,3-Dimethyluracil (1.4 g, 0.01 mol) and thiourea (IIIb) (1.52 g, 0.02 mol) were dissolved in 0.4 M sodium ethoxide (50 ml) and the solution was refluxed 18 hours and then concentrated in vacuo to a syrup. The residue was dissolved in water (50 ml) and the aqueous solution was acidified to pH~2 with concentrated hydrochloric acid. Crystalline 2-thiouracil precipitated which was collected by filtration and washed with water. The product (mp>280°, 1.2 g, 94% yield) was identical with an authentic sample of 2-thiouracil (IIb, Q=S; $R^1$, $R^2$, $R^5$, $R^6$=H) with respect to ir and uv characteristics.

In accordance with the above procedure, but where in place of thiourea there is employed N-ethylthiourea, N-butylthiourea, or N,N'-diethylurea, there is obtained 1-ethyl-2-thiouracil, 1-butyl-2-thiouracil, and 1,3-diethyl-2-thiouracil, respectively.

EXAMPLE V

Uracil from 1,3-Dimethyluracil

A mixture of 1,3-dimethyluracil (1.4 g, 0.01 mol) and urea (6.0 g, 0.1 mol) in 1 M sodium ethoxide (100 ml) was refluxed overnight with stirring. The solution was concentrated in vacuo to a syrup which was dissolved in water (40 ml). Upon acidification of the aqueous solution to pH 2 with concentrated hydrochloric acid, crystalline uracil (IIa, Q=O; $R^1$, $R^2$, $R^5$, $R^6$=H) (mp>300°, 0.7 g, 64% yield) precipitated. This product was identical with an authentic sample of uracil with respect to ir and uv spectral characteristics.

In accordance with the above procedure, but where in place of urea there is utilized $^{14}$C-urea, there is obtained 2-$^{14}$C-uracil.

EXAMPLE VI 1,3-Diethyluracil from Uracil

To a solution of uracil (28 g, 0.25 M) in aqueous sodium hydroxide (250 ml, 2N) was added diethylsulfate (45 g, 0.3 M) dropwise over a period of 30 minutes. The mixture was stirred overnight at room temperature, and then extracted with chloroform (200 ml×3). The combined extracts were washed with water (200 ml×2), dried over sodium sulfate, and evaporated to a syrup below 35° under reduced pressure. The syrup was distilled in vacuo and the fractions of boiling range 120°–140°/4 mm Hg were collected and redistilled in vacuo to collect the bp 135°/4 mm Hg fraction, 21 g, 50%. (Hilbert and Johnson, J. Am. Chem. Soc., 52, 2001 (1930) reported bp 135°/4 mm Hg. They obtained this compound by heating 1,3-diethoxypyrimidine with ethyl iodide for one week.)

In accordance with the above procedure, but where in place of diethyl sulfate there is used ditertbutyl sulfate or dibenzyl sulfate, there is obtained the corresponding 1,3-ditertbutyl uracil and 1,3-dibenzyluracil.

EXAMPLE VII

1,3-Dimethyl-ψ-uridine from ψ-Uridine

A suspension of 1.0 g ψ-uridine (I, $R^2$, $R^3$, $R^4$=H; $R^1$=β-D-ribofuranosyl; Q=O) in dimethylformamide dimethyl acetal (7 ml) was refluxed until a clear solution was obtained (30 minutes). The solution was concentrated to a syrup which was triturated with a small amount of acetone to give a solid (910 mg, 82%). Recrystallization of the crude precipitate from ethanol gave analytically pure 1,3-dimethyl-ψ-uridine mp 174° (IIa, Q=O; $R^1$=β-D-ribofuranosyl; $R^2$=H; $R^3$, $R^4$=methyl).

Analysis ($C_{11}H_{16}O_6N_2$). Calcd. C, 48.52; H, 5.92; N, 10.29. Found: C, 48.63; H, 6.02; N, 10.38.

In accordance with the above procedure, but where in place of dimethylformamide dimethyl acetal there is employed dimethylformamide diethyl acetal, there is obtained 1,3-diethyl-ψ-uridine.

EXAMPLE VIII

ψ-Isocytidine From 1,3-Dimethyl-ψ-Uridine

Guanidine hydrochloride (IIIc) (10 g, 0.1 mol) was added to 1 M sodium ethoxide in ethanol (100 ml) and the mixture was stirred at room temperature for 10 minutes and then filtered from sodium chloride. The filtrate was concentrated under vacuum below 30°. To the residue was added 1,3-dimethyl-ψ-uridine (300 mg) and the mixture heated at 80°–90° under nitrogen for 50 minutes. Water (20 ml) was added and, after removal of small amounts of insoluble impurities by filtration, the filtrate passed through a column of Amberlite IRC-50 (H+) (30×3 cm diameter) and the column washed with water. The uv absorbing fractions were collected, combined, and evaporated in vacuo to dryness, and the residue dissolved in a small amount of ethanol. Cyrstalline ψ-isocytidine (IIc′+c″) ($R^1$=β-D-ribofuranosyl; $R^2$=H) (6 mg) precipitated, mp 192°–192.5° (sintered), 193°–194° (eff.).

Analysis ($C_9H_{13}N_3O_5$). Calcd. C, 44.44; H, 5.39; N, 17.28. Found: C, 44.24; H, 5.57; N, 17.05.

The nmr spectrum of this sample taken in $D_2O$ was identical with that of beta ψ-isocytidine hydrochloride.

The mother liquor of crystallization was evaporated and the residue was dissolved in ~10% methanolic hydrogen chloride. Crystalline ψ-isocytidine hydrochloride, which precipitated out, was collected by filtration; mp 215°–216° (dec.), 185 mg (60%). The nmr, uv, and ir spectra of this sample was identical with those of authentic ψ-isocytidine hydrochloride (Chu et al, loc. cit.).

EXAMPLE IX

2-Thio-ψ-uridine from 1,3-Dimethyl-ψuridine

A mixture of 1,3-dimethyl-ψ-uridine (544 mg, 2 mmol) and thiourea (760 mg, 10 mmol) in 1 M ethanolic sodium ethoxide (20 ml) was refluxed with stirring for 2 hours. After cooling the mixture, crystalline 2-thio-ψ-uridine sodium salt (519 mg, 92%) was collected by filtration.

2-Thio-ψ-uridine sodium salt (100 mg) was dissolved in water (5 ml) and the solution was placed on a column of Amberlite IRC-50 (H+) (5×3 cm) and the column was eluted with water. Uv absorbing fractions were combined and evaporated to dryness and the solid residue was recrystallized from ethanol to give pure 2-thio-ψ-uridine (IIb) (Q=S; $R^1$=β-D-ribofuranosyl; $R^2$, $R^5$, $R^6$=H). An nmr spectrum of this sample was identical with that of an authentic sample (Chu et al, loc. cit.).

In accordance with the above procedure, but where in place of thiourea there is utilized N,N′-dibenzylthiourea, there is obtained 1,3-dibenzyl-2-thio-ψ-uridine.

EXAMPLE X

2′-Deoxy-ψ-uridine from ψ-Uridine

A mixture of ψ-uridine (10.0 g) and α-acetoxyisobutryl chloride (15.0 g) in dry acetonitrile (500 ml; dried over 4A molecular sieves) was refluxed gently for 2 hours and the solvent evaporated in vacuo. The residual syrup was dissolved in methanol (30 ml) and the solution diluted with 500 ml of ether, crude 3′-O-acetyl-2′-chloro-2′-deoxy-5′-O(2,3,5-trimethyldioxolanon-2-yl)-ψ-uridine precipitated as a syrup. After decantation of the solvent, the residue was dried in vacuo.

A mixture of this crude 2′-chloro-ψ-uridine derivative (9.0 g), with tri-n-butyltin hydride (10 g) and azoisobutyronitrile (1.0 g) in 1,2-dimethoxyethane was refluxed for 48 hours after which the solvent was removed by evaporation in vacuo. The residue was suspended in concentrated ammonium hydroxide (50 ml), the mixture stirred at room temperature for 24 hours and evaporated to a syrup in vacuo. The residue was triturated with ethanol whereupon ~1:1 mixture (4.6 g) of 2′-deoxy-ψ-uridine (IIa, Q=O; $R^1$=2′-deoxy-β-D-ribofuranosyl; $R^2$, $R^3$, $R^4$=H) and its alpha isomer crystallized. Two recrystallizations of the solid from ethanol gave the pure β-isomer (1.15 g, mp 221°–223°.

Nmr ($D_2O$): δ=2.05–2.19 (m, 2H, H-2′, H-2″), 3.64 t, 2H, H-5′, h-5″), 3.93 (m, 1H, H-4′), 4.18 (m, 1H, H-3′), 4.97 (t, 1H, H-1′), 7.58 (s, 1H, H-6).

Analysis ($C_9H_{12}N_2O_5$). Calcd. C, 47.37; H, 5.30; N, 12.18. Found: C, 47.17; H, 5.44; N, 12.45.

EXAMPLE XI

2′-Deoxy-1,3-dimethyl-ψ-uridine

A mixture of crude 2′-deoxy-ψ-uridine (1.2 g, 1:1 α/βmixture) and dimethylformamide dimethyl acetal (15 ml) was refluxed for 1.5 hours and then evporated in vacuo to a syrup which was dissolved in 5 ml of a mixture of chloroform and methanol (12:1). The solution was placed on a column of silica gel-60 (30 ×3 cm diameter) and eluted with the same solvent mixture. Two uv absorbing fractions were obtained ($R_f$ values correspond to 0.5 and 0.45 rspectively on a thin layer chromatogram coated with silica gel $G_{254}$ developed in 9:1 chloroform-methanol). Each fraction was concentrated in vacuo to dryness and the residue was crystallized from ethanol. The α-isomer of 2′-deoxyl-1,3-dimethyl-ψ-uridine (mp 171°–172°, 300 mg) was obtained from the first fraction:

Nmr ($D_2O$): δ=1.95 (m, 2H, H-2′, H-2″), 3.30 (s, NH, $NCH_3$), 3.42 (s, 3H, $NCH_3$), 3.69 (q, 1H, H-5′, $J_{44'},5'$=5.2, $J_{5',5''}$=12.4 (Hz), 3.91 (q, 1H, H-5″, $J_{4',5''}=12.4$ Hz), 4.39 (m, 1H, H-3'), 4.73 (narrow quartet of half width 2.4 Hz, 1H, H-1'), 7.73 (d, 1H, H-6, $J_{1',6}=0.5$ Hz).

Analysis ($C_{11}H_{16}N_2O_5$). Calcd. C, 51.56; H, 6.29; N, 10.93. Found: C, 51.42; H, 6.34; N, 10.99.

The β-isomer of 2'-deoxy-1,3-dimethyl-ψ-uridine (mp 136°-137°, 300 mg) was obtained from the second fraction:

Nmr (D$_2$O): δ=2.07-2.25 (m, 2H, H-2', H-2''), 3.30 (s, 3H, NCH$_3$), 3.42 (s, 3H, NCH$_3$), 3.68 (q, 1H, H-5', $J_{4',5'}=2.1$, $J_{5',5''}=13.0$ Hz), 3.83 (q, 1H, H-5'', $J_{4',5''}=0.5$, $J_{5',5''}=13.0$ Hz), 4.01 m, 1H, H-4'), 4.39 (m, 1H, H-3'), 4.99 (q, 1H, H-1', $J_{1',2'}\approx 6.4$, $J_{1',2''}\approx 9.7$ Hz), 7.13 (s, 1H, H-6).

Analysis ($C_{11}H_{16}N_2O_5$). Calcd. C, 51.56; H, 6.29; N, 10.93. Found: C, 51.26; H, 6.39; N, 10.90.

EXAMPLE XII

2'-Deoxy-ψ-isocytidine from 2'-Deoxy-1,3-dimethyl-ψ-uridine

Guanidine hydrochloride (2.5 g, 0.04 mol) was added to 4M ethanolic sodium ethoxide (20 ml), stirred at room temperature for 10 minutes, and filtered from sodium chloride. The filtrate was evaporated to dryness in vacuo below 35°. To the residue was added the beta isomer of 2'-deoxy-1,3-dimethyl-ψ-uridine (300 mg) and the mixture was heated to 90°-100° for 70 minutes. After cooling, water (20 ml) was added to the mixture. Insoluble impurities were removed by filtration, the filtrate was passed through a column of Amberlite IRC-50 (H+) (30×3 cm diameter) and the column washed with water. Uv absorbing fractions were combined and evaporated to give a white solid (300 mg). Of this solid residue, 150 mg was dissolved in water (5 ml) and the solution added to a column of Dowex 1 (OH) (100-200 mesh, 30 cm×3 cm diameter). The column was eluted with water. Fractions containing uv absorbing material were combined and evaporated to dryness in vacuo to give an α/β mixture of 2'-deoxy-ψ-isocytidine (115 mg).

The mixture (50 mg) was separated on a thin layer plate (coated with silica gel GF$_{254}$, 20×10 cm) after three developments in an isopropanolethyl acetate-water (2:2:1) system. The upper band was extracted with water. The extracts were evaporated to dryness and the residue was crystallized from methanol to give 8 mg of 2'-deoxy-ψ-isocytidine (IIb, $R^1$=2'-deoxy-β-D-ribofuranosyl; $R^2$=H). Nmr (D$_2$O): δ=2.09-2.20 (m, 2H, H-2', H-2''), 3.65 (d, 2H, H-5', H-5''), 3.95 (q, 1H, H-4''), 4.34 (m, 1H, H-3'), 4.99 (t, 1H, H-1', $J_{1',2'}\approx H_{1',2''}\approx 8$ Hz), 7.65 (s, 1H, H-6).

Analysis ($C_9H_{13}N_3O_4 \cdot H_2O$). Calcd. C, 44.08; H, 6.17; N, 17.13. Found: C, 44.32; H, 6.26; N, 16.98.

Preliminary screening tests show that 2'-deoxy-ψ-isocytidine possesses activity as an antitumor agent.

We claim:

1. A process which comprises reacting an N,N-disubstituted pyrimidine of the formula

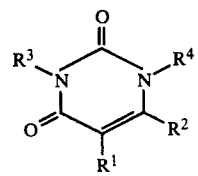

wherein $R^1$ is hydrogen, halogen, lower alkyl, phenyllower alkyl, substituted phenyllower alkyl wherein the substituent is selected from the group consisting of lower alkyl, lower alkoxy or halo; phenyl, substituted phenyl, wherein the substituents are lower alkyl, lower alkoxy or halo; or a pentosyl moiety, $R^2$ has the same value as $R^1$ and $R^1$ and $R^2$ may be the same or different provided that where $R^1$ and $R^2$ are the same, their values are other than a pentosyl moiety, $R^3$ and $R^4$ are lower alkyl, or phenyllower alkyl, or substituted phenyllower alkyl wherein the substituents are lower alkyl, lower alkoxy, or halo, wherein the term lower qualifies a moiety containing a straight or branch chain hydrocarbon moiety of 1 to 5 carbon atoms, with a nucleophile of the formula

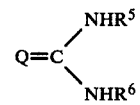

wherein $R^5$ and $R^6$ may be the same or different and are hydrogen or have the same meaning as $R^3$ above, and Q is O or S or NH, provided that where Q=NH one member of the group $R^5$ and $R^6$ is hydrogen, in the presence of a strong base to provide a pyrimidine of the formula

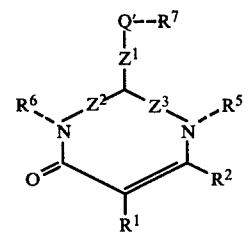

wherein where Q' is S or O,
$Z^1$ is a Q'-carbon double bond, $Z^2$ and $Z^3$ are N-carbon single bonds, and $R^7$ is absent,
and where when Q' is NH, $R^7$ is hydrogen, $Z^1$ is a N-carbon single bond, $Z^2$ is a N-carbon double bond, $Z^3$ is a N-carbon single bond and $R^6$ is absent,
or $Z^3$ is a N-carbon double bond, $Z^2$ is a N-carbon single bond and $R^5$ is absent.

2. A process of claim 1 which comprises reacting a compound of the formula

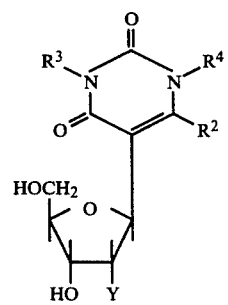

wherein Y is hydrogen or hydroxyl
with a nucleophile of the formula

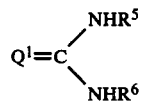

wherein $Q^1$ is O or S in the presence of a strong base, where $R^2$, $R^3$, $R^4$, $R^5$, and $R^6$ are as in claim 1.

3. A process of claim 2 wherein the base is an alkali metal alkoxide in the presence of an alkanol.

4. A process of claim 1 which comprises reacting a compound of the formula

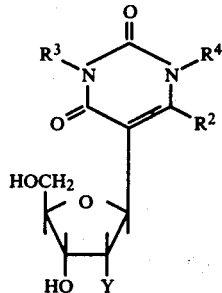

wherein Y is hydrogen or hydroxyl with a nucleophile of the formula

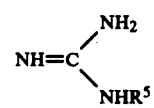

wherein $R^2$, $R^3$, $R^4$, and $R^5$ are as in claim 1.

5. A process of claim 4 wherein the nucleophile is guanidine.

6. A process of claim 5 wherein the reaction is carried out in fused guanidine at a temperature of between 60° and 120° C.

7. A process of claim 6 wherein the temperature of reaction is between 80° and 90° C.

8. A process of claim 5 wherein Y is hydrogen.

9. A process of claim 5 wherein Y is hydroxy.

* * * * *